United States Patent
Maaß et al.

(10) Patent No.: US 10,194,884 B2
(45) Date of Patent: Feb. 5, 2019

(54) REDUCING IMAGE ARTIFACTS

(71) Applicants: Nicole Maaß, Fürth (DE); Andreas Maier, Erlangen (DE); Tobias Würfl, Erlangen (DE)

(72) Inventors: Nicole Maaß, Fürth (DE); Andreas Maier, Erlangen (DE); Tobias Würfl, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/867,274

(22) Filed: Jan. 10, 2018

(65) Prior Publication Data
US 2018/0192985 A1    Jul. 12, 2018

(51) Int. Cl.
| | |
|---|---|
| A61B 6/03 | (2006.01) |
| A61B 6/00 | (2006.01) |
| A61B 90/00 | (2016.01) |
| G06T 11/00 | (2006.01) |

(52) U.S. Cl.
CPC ............. *A61B 6/583* (2013.01); *A61B 6/032* (2013.01); *A61B 6/4441* (2013.01); *A61B 6/5205* (2013.01); *A61B 6/5258* (2013.01); *A61B 90/00* (2016.02); *G06T 11/005* (2013.01); *G06T 11/006* (2013.01); *G06T 2211/412* (2013.01)

(58) Field of Classification Search
CPC .. A61B 6/00; A61B 6/03; A61B 6/032; G06T 11/003; G06T 11/005; G06T 11/006; G06T 2211/00; G06T 2211/40; G06T 2211/421; G06T 7/00; G06T 7/0002; G06T 7/0004; G06T 7/0012; G06T 2207/10081; G01N 23/046; G01N 23/083

USPC ...................................... 378/4, 901; 382/131
See application file for complete search history.

(56) References Cited

FOREIGN PATENT DOCUMENTS

| DE | 102011083643 A1 | 3/2013 |
|---|---|---|
| DE | 102013200329 A1 | 7/2014 |
| WO | 2014108237 A1 | 7/2014 |

OTHER PUBLICATIONS

Aichert, André, et al. "Epipolar consistency in transmission imaging." IEEE transactions on medical imaging 34.11 (2015): 2205-2219.
German Office Action for German Application No. 102017200282.4, dated Aug. 14, 2017.

(Continued)

*Primary Examiner* — Jurie Yun
(74) *Attorney, Agent, or Firm* — Lempia Summerfield Katz LLC

(57) ABSTRACT

A method for reducing image artifacts caused, for example, by beam hardening includes acquiring at least two projections of a transirradiated object are acquired from different perspectives by an X-ray emitter and an X-ray detector defining a projection plane. A correction model that is linear in parameters and is valid for the at least two projections is determined. At least two epipolar lines corresponding to a common epipolar plane are identified in the projection planes of the at least two projections. The parameters of the correction model are determined by optimization, taking account of data terms that are independent of the parameters. The data terms quantify a consistency condition of the at least two projections that applies to the epipolar lines. Artifact-reduced image data is determined based on the determined parameters.

17 Claims, 2 Drawing Sheets

(56) References Cited

OTHER PUBLICATIONS

Grangeat, Pierre. "Mathematical framework of cone beam 3D reconstruction via the first derivative of the Radon transform." Mathematical methods in tomography. Springer, Berlin, Heidelberg, 1991. 66-97.

Kachelrieß, Marc, Katia Sourbelle, and Willi A. Kalender. "Empirical cupping correction: A first-order raw data precorrection for cone-beam computed tomography." Medical physics 33.5 (2006): 1269-1274.

Mou, Xuanqin, Shaojie Tang, and Hengyang Yu. "A beam hardening correction method based on HL consistency." Developments in X-Ray Tomography V. vol. 6318. International Society for Optics and Photonics, 2006.

Tang, Shaojie, et al. "Data consistency condition—based beam-hardening correction." Optical Engineering 50.7 (2011): 076501-076501.

Würfl, Tobias, et al. "Epipolar Consistency Guided Beam Hardening Reduction—ECC 2." (2017).

German Grant Decision for German Application No. 10 2017 200 282.4, Grant decision Oct. 23, 2017, with English Translation.

German Office Action for German Application No. 102017200282.4, dated Aug. 14, 2017, with English Translation.

REDUCING IMAGE ARTIFACTS

This application claims the benefit of DE 10 2017 200 282.4, filed on Jan. 10, 2017, which is hereby incorporated by reference in its entirety.

BACKGROUND

The present embodiments relate to reducing image artifacts.

Imaging X-ray devices typically have X-ray tubes that serve as radiation sources. Such X-ray emitters supply X-ray radiation with a polychromatic X-ray spectrum (e.g., photons with different energies are emitted). After passing through an object under examination, the attenuated X-ray radiation is detected by an X-ray detector. Photons of higher energy, however, are in general less strongly attenuated than photons of lower energy on passing through material. This effect, in conjunction with the fact that the methods used for image reconstruction (e.g., in tomography) are based on a linear dependency between attenuation coefficients and transirradiated path length, leads to image artifacts that are designated radiation-hardening ("beam hardening") or "cupping" artifacts. Other artifacts appear in the form of stripes or as dark shadows of strongly attenuating objects or object regions in the reconstructed image.

Beam hardening artifacts occur whenever a polychromatic X-ray spectrum is used for acquiring image data. A reduction in such artifacts is therefore desirable in different technical uses (e.g., on operation of medical or material-examining imaging X-ray devices) in order to improve the image quality.

In order to reduce beam hardening artifacts, different procedures have previously been proposed that may be roughly divided into "hardware"-related and "software"-related modifications, according to approach. An apparatus or "hardware"-related approach would be, for example, to modify the X-ray emitter(s) such that only at least approximately monoenergetic X-ray radiation is emitted, to configure the X-ray detector for energy-discriminating data-acquisition or to use pre-filters. These approaches are either expensive in their realization or reduce the signal-to-noise ratio.

Method-wise modifications, by contrast, may easily be implemented with the aid of correspondingly programmable evaluating units and computer programs. A method for reducing image artifacts caused by beam hardening is described, for example, by M. Kachelrieß et al. in "Empirical cupping correction: A first order raw data pre-correction for cone-beam computed tomography," Medical Physics 33, 1269-1274 (2006). However, in order to carry out the method, an item of auxiliary information relating to the object to be recorded is to be provided, which is typically acquired through separate calibration measurements with phantoms, in the field of medical imaging, for example, with water phantoms (e.g., with water-filled reference objects).

A further approach relates to the utilization of redundancies that are present in the acquired raw data and are reflected, for example, in consistency conditions. A consistency condition of this type, which makes use, inter alia, of the principles of epipolar geometry, is described by A. Aichert et al. in "Epipolar consistency in transmission imaging," Transactions on Medical Imaging, vol. 34, No. 11, pages 2205-2219, 2015. A direct application to correction models for artifact reduction is, however, numerically complex.

DE 10 2013 200 329 A1 discloses very generally utilizing consistency conditions in order to correct image artifacts.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved method for reducing image artifacts that may be implemented efficiently is provided.

In a method for reducing image artifacts (e.g., for reducing image artifacts caused by beam hardening), at least two projections of a transirradiated object are acquired from different perspectives by an X-ray emitter and an X-ray detector defining a projection plane. According to one or more of the present embodiments, a correction model that is linear in its parameters to be optimized that is valid for the at least two projections is determined. The parameters of the correction model are formed by optimization of a cost function that may be represented as a linear combination of the parameters to be optimized and data terms that are constant with respect to the optimization. At least two epipolar lines corresponding to a common epipolar plane are identified in the projection planes of the at least two projections. From this, using a consistency condition, the data terms that are constant with respect to the parameter optimization are calculated. The parameters of the correction model are therefore determined by optimization, taking account of data terms ($a_n$) that are independent of the parameters ($w_n$). The data terms quantify a consistency condition of the at least two projections ($I_0$, $I_1$, $I_k$) that applies to the epipolar lines ($l_0$, $l_1$, $l_k$). Based on the parameters thus determined, artifact-reduced image data is determined.

In the field of X-ray imaging, it is known to record from different perspectives a plurality of projections of the object to be examined. A projection thus corresponds to the totality of the two-dimensional intensity distribution of the X-ray radiation incident on the X-ray detector or detectors acquired in a pre-determined recording geometry.

Based on the projections recorded from the different perspectives, for example, a three-dimensional reconstruction of the transirradiated object may take place. Projections recorded from different perspectives are described by cone beam geometry. The relationship between the different perspectives is described by epipolar geometry. If, for example, the X-ray emitter is moved along a trajectory for transirradiation of the object from two different directions, the locations of the X-ray emitter, then the locations of the X-ray emitter and the three-dimensional spatial coordinates of an acquired object point at the time of the recordings define an epipolar plane that intersects the projection plane pre-defined on the detector side along straight lines, the "epipolar lines". As the three-dimensional spatial coordinates of the acquired object point, for example, the isocenter may be selected. It may be shown that a consistency condition for the Radon transforms of the (error-free) projection images exists along these epipolar lines that are linked to one another (see A. Aichert et al., "Epipolar consistency in transmission imaging", Transactions on Medical Imaging, vol. 34, No. 11, pages 2205-2219, 2015).

If the projections acquired on the detector side contain any type of image artifacts, this data does not in general satisfy the consistency conditions. It has been recognized that corrected (e.g., artifact-reduced image data) may be generated in that the observance of the consistency condition is required. For this purpose, a correction model that is dependent upon parameters that are to be optimized and describes a non-linear transformation of the projection in a parameter space is to be introduced. In a borderline case, the correction model herein reflects the acquired projections exactly.

The determination of the parameters of the correction model is an optimization problem, where the consistency conditions are to be taken into account in order to obtain correction information. The direct approach not according to the present embodiments would therefore be to select and initialize correction model (e.g., any desired correction model) and to calculate an associated intermediate function (e.g., dependent upon the selected correction model). Subsequently, this correction model is to be adapted in order to calculate the intermediate function anew in the next step. This approach is therefore very complex and suitable only to a limited extent for a numerical implementation of the method.

According to one or more of the present embodiments, a correction model that is linear in its parameters is taken as a basis. Using this selection of the correction model, the optimization problem may be formulated so that the data terms to be calculated during the optimization and that, for example, take account of the consistency conditions applying to the epipolar lines, may be pre-calculated and no longer are to be adapted during the optimization. In other words, the data terms in the selected correction model may be formulated such that the data terms are independent of the parameters to be optimized and are therefore to be calculated once at the start of the actual optimization routine. This procedure enables the method to be implemented efficiently since the required calculation effort is significantly reduced as compared with the direct approach.

The method of one or more of the present embodiments may therefore be implemented with the aid of suitably configured evaluating units since the correction information may be determined based on image raw data that may be provided by per se known X-ray devices. The method proposed by the present embodiments also does not distinguish, on occurrence of inconsistencies in the acquired image raw data, with regard to source, so that in principle, a reduction in image artifacts of different origin is enabled. Through the formulation of the consistency condition in the Radon space, the numerical effort is minimized.

The parameters of the correction model that are to be optimized may be determined by methods of convex (e.g., linear) optimization.

The cost function may be formed taking account of a consistency condition applying to the epipolar lines and linking the derivatives of the 2-D Radon transforms of the at least two projections to one another.

In an exemplary embodiment, a pixelwise independent correction model is used (e.g., the parameter space spanned by the correction model is given by a linear combination of basis functions that are determined by transformation of the scanned projections).

In one embodiment, a polynomial correction model is used (e.g., the basis functions spanning the parameter space are, for example, polynomials or monomials). For example, monomials may be selected as basis functions that are combined to a polynomial, where the parameters of the correction model are included as weights of the individual monomials. For each of the parameters to be optimized, two-dimensional projection data dependent upon this factor may be separately transformed, and intermediate functions may be formed by Radon transforms and derivative formation (see A. Aichert et al., "Epipolar consistency in transmission imaging," Transactions on Medical Imaging, vol. 34, No. 11, pages 2205-2219, 2015). From the intermediate functions, data terms independent of the parameters to be optimized may then be calculated.

In an embodiment, the correction model is defined by the relation $$f(I_k, w) = \sum_{n=1}^{N} w_n I_k^n$$

Variables shown bold denote vectors. The parameters to be optimized are denoted by w or $w_n$. The intensity distributions acquired in the individual projections are given by $I_k^n$, where the index k numbers the projections recorded from different directions. Monomials have been selected as basis functions (e.g., the basis function $I_k^n$ describes the nth power of the pixelwise independently transformed projection $I_k$). For such a correction model, it has been found that the consistency conditions to be required based on the epipolar geometry may be expressed as a relationship between the Radon transforms of the basis function $I_k^n$. This relationship therefore no longer explicitly depends on the parameters and therefore no longer needs to be updated on solving the optimization problem.

A plurality of epipolar planes may be pre-defined in the at least two projections, each containing the connecting line that connects the positions of the X-ray emitter(s) at the time point of the recording. In other words, a whole family ("pencil") of epipolar planes may be identified for two projections in each case.

In one embodiment, therefore, a plurality of epipolar lines corresponding respectively pairwise to common epipolar planes are identified in the projection planes of the at least two projections, and the parameters to be optimized of the correction model are determined taking account of data terms applying to the respectively pairwise associated epipolar lines.

In general, particularly for tomographic methods, a plurality of projections is acquired from different perspectives. In a development of one or more of the present embodiments, a plurality (e.g., all) projections may be used for image correction. Therefore, more than two projections of the transirradiated object are acquired from different perspectives by the X-ray emitter and the X-ray detector, and two epipolar lines corresponding to a common epipolar plane are identified in the projection planes of the at least two projections associated respectively pairwise with one another. The parameters to be optimized of the correction model are determined taking account of the consistency condition applying to the acquired projections. In this regard, the correction model that is linear in its parameters to be optimized may reflect the totality of the projections acquired.

The method described above supplies artifact-reduced image data that is used, for example, for three-dimensional reconstruction of the object. The correction of the image data may herein take place on the plane of the corrections or on the plane of the three-dimensional image data.

In another example, an imaging X-ray device with at least one X-ray emitter and at least one X-ray detector that are configured to acquire at least two projections of a transirradiated object from different perspectives is provided. The imaging X-ray device has an evaluating unit that is configured for determining artifact-reduced image data by optimizing a correction model that applies for the at least two projections, according to the method described above.

The imaging X-ray device may be, for example, a medical X-ray device (e.g., a computed tomography device, a mammography device or a C-arm X-ray device). The imaging X-ray device may be configured for tomography. In other cases, the imaging X-ray device is a material-examining X-ray device. Other embodiments relate to X-ray devices for dentistry, X-ray devices for luggage examination, or industrial X-ray devices (e.g., for transilluminating freight containers).

The computational steps of the method described above for reducing image artifacts may be implemented as a computer routine in a non-volatile storage medium of the evaluating unit.

The X-ray detector defining the projection plane may be, for example, a flat panel detector.

For the recording of the projections from the different perspectives, one or more X-ray emitters and/or one or more X-ray detectors that have similar (e.g., identical) spectral properties may be provided. The X-ray emitter and X-ray detector, as with C-arm X-ray devices, may be connected rigidly to one another or may be placeable freely relative to one another.

In one embodiment, the at least one X-ray emitter and/or the at least one X-ray detector are movable along a pre-defined or pre-definable trajectory.

BRIEF DESCRIPTION OF THE DRAWINGS

FIG. 1 is an imaging X-ray system;

FIG. 2 is an illustration of the epipolar geometry;

DETAILED DESCRIPTION

Figure 3:
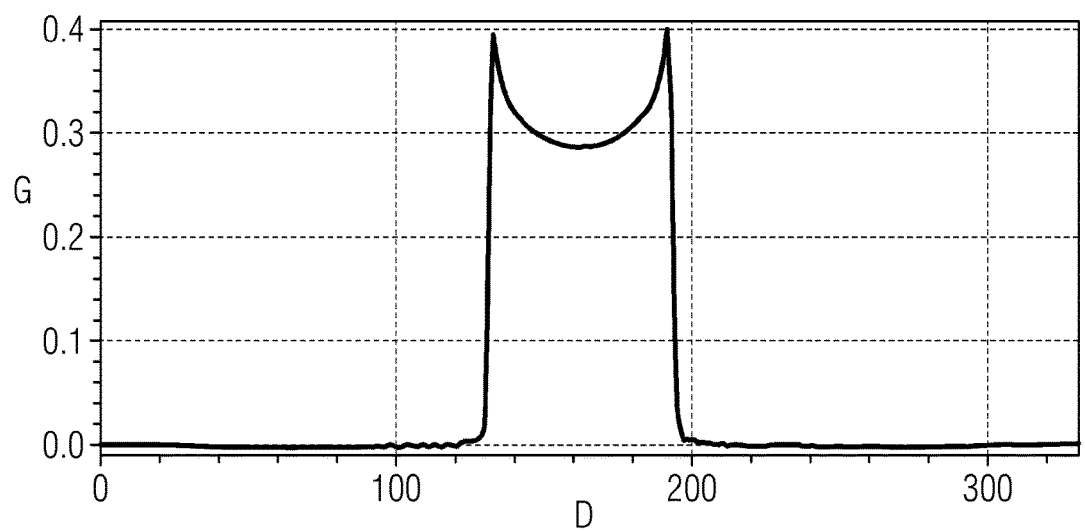
FIG. 3 is a gray value diagram of a massive object that contains artifacts that are caused by beam hardening.

Parts or reference quantities that correspond to one another are provided with the same reference signs in all the drawings.

Figures 1, 2:
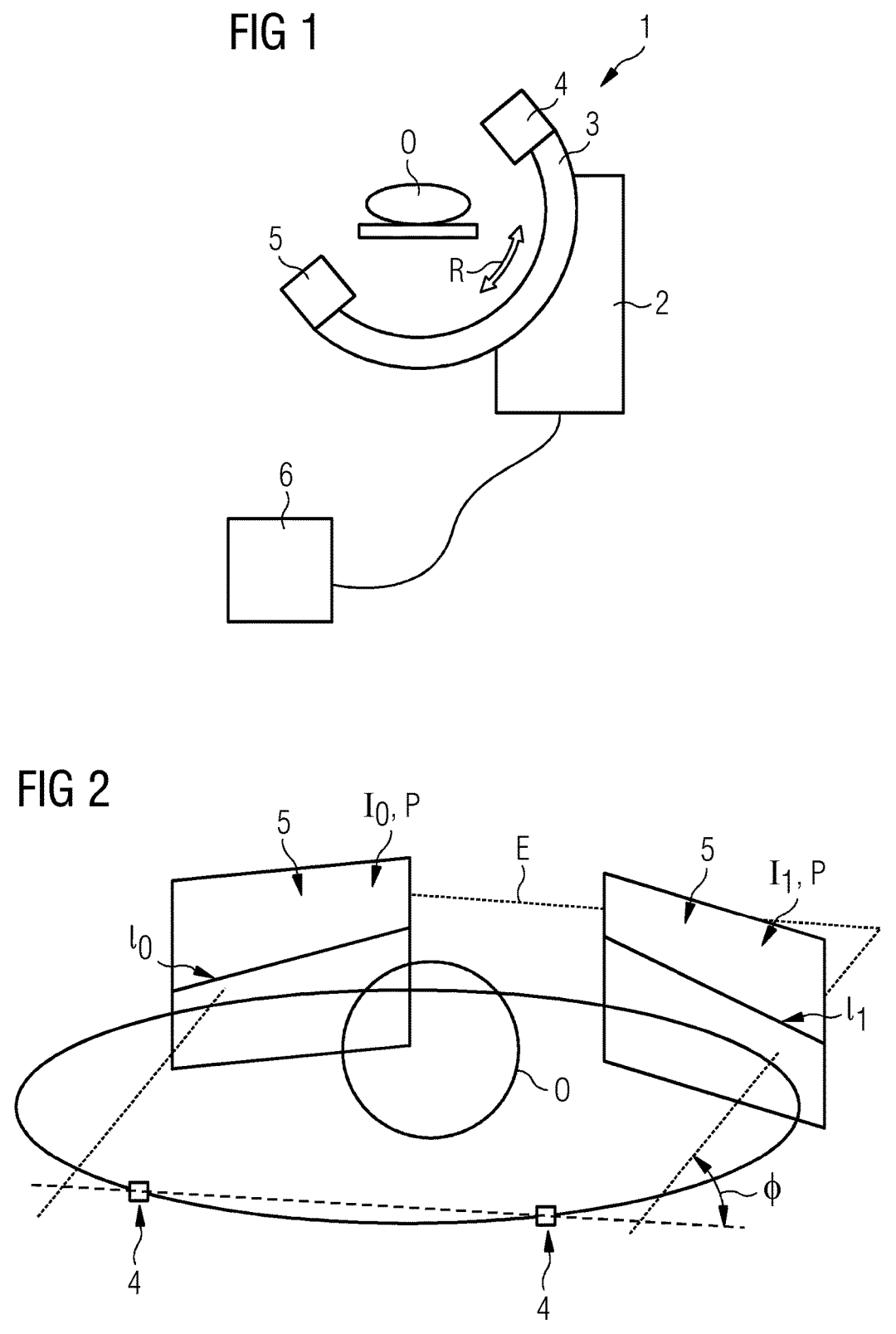

FIG. 1 shows, in a schematic representation, an imaging X-ray device 1 that is configured to carry out the method provided by one or more of the present embodiments. Shown purely by way of example is an X-ray device configured as a C-arm X-ray device with a holder 2 for a C-arm 3 that carries an X-ray emitter 4 and an X-ray detector 5. The C-arm 3 is movably guided in the holder 2 so that, for example, orbital rotations R about a body region of a patient to be examined who is placed on a patient support 6 may be carried out. The X-ray emitter 4 and the X-ray detector 5 may thus be arranged in relation to an object O lying therebetween such that projections may be acquired from different perspectives.

The X-ray device 1 further includes an evaluating unit 6 that is connected to the X-ray detector such that acquired image raw data are feedable to the evaluating unit. The acquired image raw data generally contain image artifacts (e.g., beam hardening artifacts are generated if X-ray emitters 5 with a polychromatic spectrum are used). Such artifacts typically have an appearance that is illustrated schematically in FIG. 3. What is shown is the acquired gray values G as a function of the distance D, which correspond to the recording of an at least approximately homogeneously massive object O. The beam hardening leads to a lower attenuation occurring in the interior of the object O than at the edge. The image of the object O reconstructed from uncorrected image raw data appears denser in the edge region than in the interior. This effect is designated the "cupping" artifact.

For a recording geometry that corresponds to the epipolar geometry shown schematically in FIG. 2, such artifacts may be corrected efficiently. For this purpose, for example, the X-ray emitter 4 and the X-ray detector 5 are moved on a circular path round the object O, and, at least at two time points, recordings of the object are made from different perspectives. The X-ray detector 4 herein defines a projection plane P. Respectively acquired projections $I_k$ are numbered by the index k, and the intensity distribution of the recordings acquired at the two time points thus corresponds (for k=0, 1) to the projections $I_0$, $I_1$.

The locations of the X-ray emitter 4 at the time point of the recording together with an object point of the object O therefore define an epipolar plane E (shown dotted) that the projection planes P each intersect along epipolar lines $l_k$ or (for k=0, 1) along epipolar lines $l_0$, $l_1$. For the recording geometry shown in FIG. 2, there is a plurality of epipolar planes E that are produced through rotation of the epipolar plane E, shown dashed, about the connecting straight line given by the locations of the X-ray detector 4 through the angle $\phi$.

It has been shown that for the Radon transforms r of the ideal (e.g., error-free) projection data $I_0^{id}$, $I_1^{id}$, a consistency condition defined, in each case, along two mutually corresponding epipolar lines applies:

$$\frac{d}{dt}\rho_{I_0^{id}}(l_0) \approx \frac{d}{dt}\rho_{I_1^{id}}(l_1)$$

This is utilized in order to correct the actually acquired projections $I_0$, $I_1$. For this purpose, a correction model $f(I_k, w)$ is assumed, where the totality of the parameters $w_n$ of a vector w is described. With this, an optimization problem may be formulated in which the correction model $f(I_k, w)$ is to fulfill the relation $$\frac{d}{dt}\rho_{f(I_0,w)}(l_0) \approx \frac{d}{dt}\rho_{f(I_1,w)}(l_1)$$

However, the direct evaluation of this problem is numerically burdensome since the Radon transform $\rho$ is to be calculated anew for each iteration step of the optimization.

As a solution approach, it is proposed specifically to select a polynomial correction model that is linear in its parameters $w_n$ to be optimized. A possible correction model that is particularly simple to evaluate is given by $$f(I_k, w) = \sum_{n=1}^{N} w_n I_k^n$$

This non-linear correction model f is linear in the parameters $w_n$. The basis functions $I_k^n$ describe the nth power of the pixelwise independently transformed projection $I_k$. With this selection, the optimization problem may be defined as follows: find parameters $w_n$ such that $(\Sigma_{n=1}^{N} w_n a_n)^2$ is minimized, where $$a_n = \frac{d}{dt}\rho_{I_0^n}(l_0) - \frac{d}{dt}\rho_{I_1^n}(l_1)$$

remain constant as data terms during the optimization. The data terms $a_n$ are calculated from the intermediate functions $$\frac{d}{dt}\rho_X(l)$$

where X is a two-dimensional projection image. The remaining problem may therefore be solved efficiently by methods of convex (e.g., linear) optimization. The scaling may be specified, for example, in that it is to be provided that a gray value of a selected image point assumes the same value in the projections $I_0$, $I_1$, $I_k$ before and after the correction.

Figure 4:
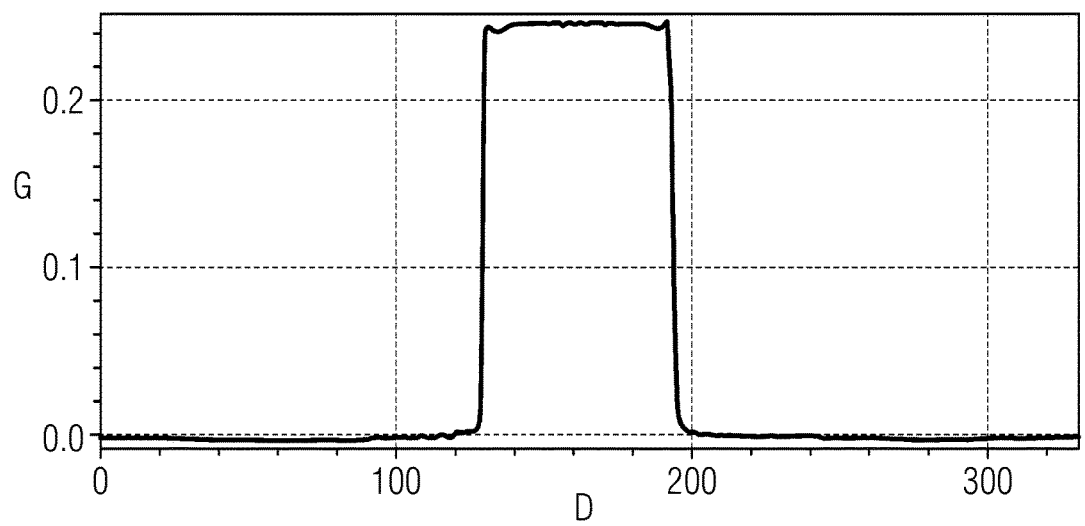
FIG. 4 is the gray value diagram of FIG. 3 following image correction according to the method proposed by the present embodiments.

FIGS. 3 and 4 illustrate schematically the reduction in image artifacts achievable with the method based on gray value diagrams for a massive object. What is shown is the gray value G of image points as a function of the distance D. It is apparent that the "cupping" artifact still present in FIG. 3 is severely reduced or is no longer to be seen. The artifact-reduced image data corresponds to the values of the correction model f with optimum values for the parameters $w_n$ and may be used, for example, for tomographic reconstruction of the acquired object O.

The method described above may be applied directly to as many projections $I_k$ and/or epipolar planes E as desired, or extended. As described above, for two projections ($I_0$, $I_1$, $I_k$), in each case, there is a set of epipolar planes E that may be used according to the above described method for image correction.

Although the invention has been illustrated and described in detail by reference to the exemplary embodiments, the invention is not restricted thereby. Other variations and combinations may be derived therefrom by a person skilled in the art without departing from the essential concept of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for reducing image artifacts, wherein at least two projections of a transirradiated object are acquired from different perspectives by an X-ray emitter and an X-ray detector defining a projection plane, the method comprising:

determining a correction model that is linear in parameters to be optimized, the correction model being valid for the at least two projections;

identifying at least two epipolar lines corresponding to a common epipolar plane in the projection planes of the at least two projections;

determining the parameters of the correction model, the determining of the parameters of the correction model comprising optimizing the correction model taking account of data terms that are independent of the parameters, the data terms quantifying a consistency condition of the at least two projections that applies to the epipolar lines; and determining artifact-reduced image data based on the determined parameters.

2. The method of claim 1, wherein determining the parameters comprises optimizing using convex optimization.

3. The method of claim 2, wherein the convex optimization comprises a linear optimization.

4. The method of claim 1, further comprising forming a cost function taking account of a consistency condition applying to the epipolar lines for derivatives of 2-D Radon transforms of the at least two projections.

5. The method of claim 1, wherein the correction model is a pixelwise independent correction model.

6. The method of claim 1, wherein the correction model is a polynomial correction model.

7. The method of claim 1, wherein the correction model is a pixelwise independent correction model and a polynomial correction model, and wherein dependent upon the parameters to be optimized, the correction model f assumes the form $f(I_k, w) = \Sigma_{n=1}^{N} w_n I_k^n$, and wherein basis functions ($I_k^n$) describe the nth power of the pixelwise independently transformed projection ($I_k$).

8. The method of claim 1, further comprising:

identifying a plurality of epipolar lines corresponding respectively pairwise to common epipolar planes in the projection planes of the at least two projections, wherein determining the parameters of the correction model comprises determining the parameters to be optimized of the correction model taking account of the data terms formed from the respectively pairwise associated epipolar lines.

9. The method of claim 1, wherein more than two projections of the transirradiated object are acquired from different perspectives by the X-ray emitter and the X-ray detector, and wherein two epipolar lines corresponding to a common epipolar plane are identified in the projection planes of two projections associated, respectively pairwise, with one another.

10. The method of claim 1, wherein the artifact-reduced image data is used for tomographic reconstruction of the object.

11. An imaging X-ray device comprising:

at least one X-ray emitter and at least one X-ray detector that are configured to acquire at least two projections of a transirradiated object from different perspectives; and a processor that is configured to determine artifact-reduced image data, the determination of the artifact-reduced image data comprising optimization of a correction model that applies for the at least two projections, the determination of the artifact-reduced image data comprising:

determination of a correction model that is linear in parameters to be optimized, the correction model being valid for the at least two projections;

identification of at least two epipolar lines corresponding to a common epipolar plane in the projection planes of the at least two projections;

determination of the parameters of the correction model, the determination of the parameters of the correction model comprising optimization of the parameters taking account of data terms that are independent of the parameters, the data terms quantifying a consistency condition of the at least two projections that applies to the epipolar lines; and determination of artifact-reduced image data based on the determined parameters.

12. The imaging X-ray device of claim 11, wherein the at least one X-ray emitter, the at least one X-ray detector, or the at least one X-ray emitter and the at least one X-ray detector are movable along a pre-defined or pre-definable trajectory.

13. The imaging X-ray device of claim 11, wherein determination of the parameters comprises optimization using convex optimization.

14. The imaging X-ray device of claim 13, wherein the convex optimization comprises a linear optimization.

15. The imaging X-ray device of claim 11, wherein the processor is further configured to form a cost function taking account of a consistency condition applying to the epipolar lines for derivatives of 2-D Radon transforms of the at least two projections.

16. The imaging X-ray device of claim 15, wherein the correction model is a pixelwise independent correction model.

17. The imaging X-ray device of claim 11, wherein the correction model is a polynomial correction model.

* * * * *

UNITED STATES PATENT AND TRADEMARK OFFICE
CERTIFICATE OF CORRECTION

PATENT NO. : 10,194,884 B2
APPLICATION NO. : 15/867274
DATED : February 5, 2019
INVENTOR(S) : Nicole Maaß, Andreas Maier and Tobias Würfl Page 1 of 1

It is certified that error appears in the above-identified patent and that said Letters Patent is hereby corrected as shown below:

On the Title Page

Add item (30) Foreign Application Priority Data
January 10, 2017 (DE) ......................102017200282.4

Signed and Sealed this
Ninth Day of April, 2019

Andrei Iancu
*Director of the United States Patent and Trademark Office*